United States Patent [19]

Katayama, deceased et al.

[11] Patent Number: 5,366,661
[45] Date of Patent: Nov. 22, 1994

[54] METHOD FOR FORMING A STABILIZED AQUEOUS DISPERSION OF INORGANIC PARTICLES OR ORGANIC PARTICLES FOR FOOD STUFFS

[75] Inventors: Sakae Katayama, deceased, late of Nishinomiya, by Hirohiko Katayama, executor; Atsushi Tsuda, Takatsuki; Kenzi Hanno, Hirakata, all of Japan

[73] Assignee: Katayama Chemical, Inc., Osaka, Japan

[21] Appl. No.: 892,326

[22] Filed: Jun. 2, 1992

Related U.S. Application Data

[63] Continuation-in-part of Ser. No. 866,091, Apr. 6, 1992, abandoned, which is a continuation of Ser. No. 598,806, Oct. 12, 1990, abandoned, which is a continuation of Ser. No. 215,632, Jul. 6, 1988, abandoned.

[30] Foreign Application Priority Data

Jul. 27, 1987 [JP] Japan ................ 62-188639

[51] Int. Cl.$^5$ ............ A23J 3/18; A23J 3/30; B01F 17/30; B01J 13/00
[52] U.S. Cl. ................ 252/314; 71/DIG. 1; 252/311; 252/313.1; 252/356; 426/656; 514/937; 530/372; 530/374; 530/375
[58] Field of Search .............. 252/313.1, 314, 356, 252/311; 426/656; 530/372, 374, 375

[56] References Cited

U.S. PATENT DOCUMENTS

| | | | |
|---|---|---|---|
| 1,245,983 | 11/1917 | Satow | 530/372 X |
| 2,090,537 | 8/1937 | Lund | 252/356 X |
| 2,119,872 | 6/1938 | Wiegand | 252/356 X |
| 2,232,052 | 2/1941 | Cummins | 252/356 X |
| 2,271,499 | 1/1942 | Rice | 530/374 X |
| 2,431,256 | 11/1947 | Keil et al. | 252/356 X |
| 2,434,874 | 1/1948 | Tucker et al. | 530/374 X |
| 2,582,965 | 1/1952 | Coffman | 530/374 |
| 3,127,388 | 3/1964 | Johnson et al. | 530/372 X |
| 3,394,119 | 1/1968 | Luce et al. | 252/356 X |
| 3,653,912 | 4/1972 | Koski et al. | 426/656 X |
| 3,769,030 | 10/1973 | Kleinert | 426/656 X |
| 3,770,452 | 11/1973 | Finley | 426/656 X |

FOREIGN PATENT DOCUMENTS

| | | | |
|---|---|---|---|
| 0148600 | 7/1985 | European Pat. Off. | 426/656 |
| 45-29423 | 9/1970 | Japan . | |
| 46-28157 | 8/1971 | Japan . | |
| 50-95443 | 7/1975 | Japan . | |
| 53-66473 | 6/1978 | Japan . | |
| 0187174 | 11/1983 | Japan | 426/656 |
| 60-237939 | 11/1985 | Japan . | |
| 61-81464 | 4/1986 | Japan . | |

*Primary Examiner*—Richard D. Lovering
*Attorney, Agent, or Firm*—Bryan Cave

[57] ABSTRACT

A method for forming a stabilized aqueous dispersion which is useful for reducing viscosity of a stabilized aqueous dispersion wherein various water-insoluble or sparingly soluble inorganic and/or organic particles for food stuffs are suspended, accelerating suspension and dispersion of the various particles, and preventing sedimentation of the suspended particles.

10 Claims, No Drawings

METHOD FOR FORMING A STABILIZED AQUEOUS DISPERSION OF INORGANIC PARTICLES OR ORGANIC PARTICLES FOR FOOD STUFFS

This is a continuation-in-part of U.S. application Ser. No. 07/866,091, filed on Apr. 6, 1992 now abandoned, which is a continuation of Ser. No. 07/598,806, filed on Oct. 12, 1990 (now abandoned), which in turn is a continuation of Ser. No. 07/215,632, filed on Jul. 6, 1988 (now abandoned).

BACKGROUND OF THE INVENTION

1. Field of the Invention

The present invention relates to a method for forming a stabilized aqueous dispersion of inorganic and/or organic particles for food stuffs. More particularly, the invention relates to a method for forming a stabilized aqueous dispersion which is useful for reducing viscosity of aqueous dispersions wherein various water-insoluble or sparingly soluble inorganic and/or organic particles for food stuffs are suspended, accelerating suspension and dispersion of the various particles, and preventing sedimentation of the suspended particles.

2. Description of the Prior Art

Aqueous dispersions wherein various organic and/or inorganic particles are suspended in aqueous medium are used for various purposes. The organic and/or inorganic particles, the subjects to be dispersed, are, for example, those organic particles for food stuffs, such as cocoa powder, fruit pulp, solid matters of miso (bean paste), solid matters of soup, etc., as well as those inorganic particles such as calcium carbonate, sachin white, talc, red oxide, magnesium hydroxide, zinc white, barium sulfate, kaolin, clay, etc. As actual embodiments of the aqueous dispersions, there can be mentioned paint & varnish; fillers; neutralizing agents for desulfurization of exhausted smoke; material dispersions for ceramics; various food stuffs such as juice, chocolate milk, chocolate syrup, cocoa, miso soup, soup, zenzai (thick red bean-meal soup with sugar), shiruko (red-bean soup with sugar), etc; cosmetics such as pigment-containing foundation, milky lotion, etc.; pharmaceutical medicines such as emulsion, suspension, contrast medium, etc.; quasi-drug such as toothpaste, etc.; and the like.

Such various aqueous dispersions may be in the form of a liquid or slurry, depending on the property and amount of the suspended particles. When the particle-concentration is high, the aqueous dispersion becomes, in many cases, a slurry having a high viscosity, which is difficult to handle on use, transportation, storage, etc. Further, in some cases, the state of suspension of the particles is unstable and the particles gradually precipitate and finally separate.

Therefore, with the purpose of reducing the viscosity of the aqueous dispersions in slurry state and maintaining stability of the suspension of particles, a method of adding polyphosphates, polymers or copolymers of acrylic or methacrylic acid series, or their salts to such dispersions has been hitherto effected, and these additives are in general called a particle-dispersing agent. It has also been proposed recently to use maleic acid (or fumaric acid)/acrylic acid (or methacrylic acid) copolymers and acrylic acid (or methacrylic acid) copolymers, as a particle-dispersing agent for inorganic pigments dispersions (Japanese Unexamined Patent Publication No. Sho 61-81464).

On the other hand, in the field of food stuffs, miso soup, shiruko, zenzai, cocoa, soup, etc., are frequently sold in the form of dry powder, i.e., the so-called instant food stuffs, because of the preservability and the easiness of handling. However, there has been a problem of dispersibility of the powder or the contents in these food stuffs. For example, by merely pouring hot water into an instant miso soup, it was found that the suspended miso particles precipitated within a shorter time compared to using raw miso. Also with respect to other instant food stuffs, it was difficult to disperse the contents with water or chilled water within a short time.

Various beverages and dairy products such as milk are often commercially available in the form of mixture with a calcium compound for enriching calcium component, such as calcium carbonate, calcium pantothenate, calcium acetate or the like. However, when such products are stocked for a long time, a calcium precipitate occurs and hence deteriorates rates the qualities of the products as commercial goods.

To remove such a problem or difficulty, it has been proposed to add sucrose/fatty acid esters, sorbitan/fatty acid esters, or the like to instant food stuffs (Japanese Patent Publications No. Sho 46-28157 and No. Sho 45-29423, Japanese Unexamined Patent Application No. Sho 53-66473, etc.).

Also in the field of agricultural chemicals, there has been an inconvenience that, when the active ingredient was a solid sparingly soluble in water, the flowable preparation (aqueous suspension) prepared caused aggregation and/or separation of the active ingredient particles or, when such preparation or a wettable preparation was diluted with water, the active ingredient particles and the carrier precipitated. Therefore, nonionic, anionic, cationic or other surface active agents and viscosity-increasing agents such as CMC (carboxymethylcellulose), PVA (polyvinylalcohol), etc., have been hitherto used.

Particle-dispersing agents comprising, for example, the above-mentioned polymers of polyphosphoric acid series, polyacrylic acid series or other series or the widely used surface active agents cannot be said completely harmless against human bodies, animals and plants, and accordingly there is a limitation in their application to aqueous dispersions used for food stuffs, cosmetics, agricultural chemicals and pharmaceutical medicines. On the other hand, the above-mentioned sucrose/fatty acid esters, etc., have been used as a dispersing agent for not only food stuffs but also cosmetics, pharmaceutical medicines, etc. However, there has been a problem that their particle-dispersing effect was insufficient and, in addition, they were economically disadvantageous.

The purpose of the present invention resides in providing a particle-dispersing agent which is quite safe and harmless, even when it is taken in the human body, which does not cause any environmental pollution or any damage on plants because of its good susceptibility for biolysis, even when it is discharged into a river or the like, and which has yet an excellent particle-dispersing effect.

Various reports have been hitherto made as to the properties of grain partial degradation products, especially of hydrolyzates by acid or enzyme. However, any description of their particle-dispersing action is not given in the reports, as far as we know. For example, it is described in Japanese Unexamined Patent Publication No. Sho 50-95443 that the sightly acidic gluten powder obtained by acidifying wheat gluten under a pH of 2.0–6.0 is superior as an additive for food materials, compared with one obtained by treatment with a reducing agent. In this Publication, however, any concrete effect as to the additive is not disclosed at all. Further, in Japanese Unexamined Patent Publication No. Sho-60-237939, partially hydrolysed wheat gluten obtained by hydrolysis of wheat gluten with enzyme is disclosed, and there is set forth a disclosure to the effect that the partially hydrolysed wheat gluten can be used as a substitute for caseinates in the production of imitations of cheese. However, any disclosure is not given in this Publication, as to particle-dispersing agents.

U.S. Pat. No. 2,582,965 (Coffman et al) discloses that a decomposition product of wheat gluten hydrolyzed with quick lime is more effective as a protective colloid agent for polymer emulsion compared to casein, but does not disclose that such decomposition product is effective as a particle-dispersing agent for food stuffs, however, has never been disclosed.

SUMMARY OF THE INVENTION

Thus, the present invention provides a method for forming a stable dispersion of water insoluble inorganic and/or organic particles for food stuffs, which comprises mixing in an aqueous medium the particles with a grain protein partially degraded by
  (i) a single degradation with either one of alkali, acid, proteinase, reducing agent and oxidizing agent, or
  (ii) a combination of two kinds of degradations each with acid, proteinase, reducing agent or oxidizing agent,
and having a weight average molecular weight of 500–110000.

DETAILED DESCRIPTION OF THE PREFERRED EMBODIMENT

The aqueous medium as used in the specification means water, milk or edible solutions containing water as main component.

The protein partial degradation products used in the present invention are suitably those having a weight average molecular weight Mw of 500–110000 as determined according to the Gel filtration method, and those having a Mw of 700–100000 are preferred in view of the particle-dispersing effect. With a Mw of less than 500, protein partial degradation products consist substantially of amino acids and oligomers thereof and accordingly are not suitable because of their low particle-dispersing effect. On the other hand, with a Mw of more than 110000, protein partial degradation products approach the undegraded protein in their properties and accordingly are not suitable because of their low particle-dispersing effect. By the way, the molecular weights here are determined according to the Gel filtration method using sodium polystyrenesulfonates having a molecular weight of 1600, 6500, 16000, 65000 or 88000, as the standard substance, and Sephadex G-75 or G-100 (from Pharmacia Ltd.) as the carrier.

In the present invention, the term "grain protein" means a protein contained in grain, and the "grain" here means the seed of wheat and barley, corns (for example, maize), beans (for example, soya beans) and the like. Among proteins contained in such grains, wheat protein contains glutenin and gliadin as the main components and is usually called wheat gluten, and maize protein contains zein as the main component and is usually called maize gluten. Each is a known substance which can be obtained from the corresponding grain by separation and extraction according to the usual manner. For example, to obtain wheat protein (wheat gluten), wheat flour is kneaded stiffly by adding a small amount of water and then kneaded in a large amount of water whereby starch is suspended in water and the gluten-containing portion remains as a sticky lump. By repeating this operation several times while replacing the water, wheat protein is obtained as a grayish brown sticky lump. For the preparation of the partial degradation products of the present invention, although such lump can be used as it is, a product obtained by drying, further purifying or partial modifying of the lump may also be used. Wheat gluten is commercially available in the form of dry powder. Other commercially available maize gluten, soya bean protein, etc., may also be used as convenient.

These proteins may be used in the form of either crude products or purified products. However, it is preferable to use a product containing the protein in an amount of 70% or more.

The partial degradation products of the present invention can be prepared by subjecting the above-mentioned grain protein to a degradation treatment with an alkali, acid, proteinase, reducing agent or oxidizing agent.

The above degradation treatment with an alkali is suitably effected by heating grain protein in a dilute aqueous alkaline solution. Usually, it is suitable to heat an aqueous solution or dispersion of grain protein to be degraded at ca. 60°–180° C. for ca. 10–600 minutes while stirring in the presence of an alkaline agent such as sodium hydroxide, potassium hydroxide, calcium hydroxide, sodium carbonate, potassium carbonate, etc. As the aqueous solution or dispersion of grain protein to be degraded, one containing 2–40% (by weight) of the subject is preferably used. The amount of an alkaline agent used is preferably 0.1–6 g per 20 g of the subject to be degraded.

The degradation treatment with acid is suitably effected by heating grain protein in a dilute aqueous acid solution. Usually, it is suitable to heat an aqueous solution or dispersion of grain protein to be degraded at ca. 60°–120° C. for ca. 10–60 minutes while stirring in the presence of an inorganic acid such as hydrochloric acid, sulfuric acid, etc., or an organic acid such as acetic acid, etc. The quantitative conditions here are preferably the same as those mentioned above for the alkaline hydrolysis.

The degradation treatment with proteinase is suitably effected in a dilute aqueous solution of an enzyme having protease activity. Usually, it is effected by keeping an aqueous solution or dispersion of grain protein to be degraded at ca. 10°–60° C. for ca. 60–600 minutes in the presence of a small amount of an enzyme such as pepsin, alkali protease, papain, etc., under the optimal pH condition for the enzyme. The quantitative conditions here are preferably the same as those described above, except that 0.02–5 g of the enzyme is used per 20 g of grain protein to be degraded.

The degradation treatment with reducing agent or oxidizing agent is suitably effected in a dilute aqueous solution of the reducing agent or the oxidizing agent. Usually, it is effected by keeping an aqueous solution or dispersion of grain protein to be degraded at ca. 10°–100° C. for 10–600 minutes in the presence of a small amount of a reducing agent such as a sulfite, a thiol compound, erythorbic acid, hydrazine, etc., or an oxidizing agent such as hydrogen peroxide, a hypochlorite, etc. The quantitative conditions here are preferably the same as those described above, except that 0.1–5 g of the reducing agent or the oxidizing agent is used per 20 g of grain protein to be degraded.

In the present invention, not only a partial degradation product obtained by a single degradation with either one of the above-mentioned alkali, acid, proteinase, reducing agent and oxidizing agent, but also a partial degradation product obtained by a combination of two kinds of degradations each with the above-mentioned acid, proteinase, reducing agent or oxidizing agent, can be used. The combination of two kinds of degradations is shown concretely by Examples given hereinafter.

Although the solution containing a grain protein partial degradation product thus obtained can be used as it is, as a particle-dispersing agent, it is also possible to use the grain protein partial degradation product in the form of powder which is obtained by drying the solution. On using the protein partial degradation product as a particle-dispersing agent, the amount of addition may very depending on the kind, concentration, purpose, etc., of the aqueous dispersion to which it is applied. However, it is usually preferred to add the protein partial degradation product in the amount of 0.02–20% (by weight) per suspended particles, in view of the dispersion stability. By adding the protein partial degradation product in such a concentration, it is possible on the basis of its dispersing effect to reduce the viscosity of various aqueous dispersion which are in highly viscous slurry state, or to prevent sedimentation of the suspended particles in unstable aqueous dispersions and obtain aqueous dispersions whose state of suspension is stabilized.

For example, it is possible, by addition of a small amount of the protein partial degradation product, to reduce the viscosity of a calcium carbonate slurry containing 50% (by weight) of calcium carbonate and the viscosity of a kaolin slurry containing 60% (by weight) of kaolin, each to 6000 cps or less.

Further, it is possible, by addition of the protein partial degradation product to edible water insoluble organic particles (i.e., powdery food stuffs) such as cocoa powders, or solid matters of miso (bean paste), instant soup, instant zenzai or instant shiruko, etc., to accelerate dispersion of the contents of the powdery food stuffs into water and prevent sedimentation of the suspended particles (solid matters) for a long time. Also, in case where the protein partial degradation product is added to milk which is enriched with a calcium component as water-insoluble inorganic and/or organic particles, it can prevent to precipitate the calcium component.

Thus, the protein partial degradation product is useful, because of its non-toxic, odorless and tasteless properties, not only as a particle-dispersing agent for reducing viscosity or a particle-dispersing agent for stabilizing suspensions in the fields of various food stuffs containing the above-described powdery food stuffs, cosmetics, pharmaceutical medicines, etc.

With the particle-dispersing agents for food stuffs of the present invention, various other additives (for example, surface active agents, preservatives, other dispersing agents, etc.) which do not interfere with its effect may be included in accordance with its use. Especially, other kinds of dispersing agents and viscosity-increasing agents, such as gum arabic, pectin, CMC, gum xanthenic, alginic acid, other polysaccharides, etc., may co-exist in the particle-dispersing agents for food stuffs of the present invention. Further, other synthetic high molecular weight compounds such as polyacrylic acid, polyvinyl alcohol, etc., and various conventionally used surface active agents may also be used in the particle-dispersing agents for food stuffs of the present invention.

Particularly when the particle-dispersing agents for food stuffs are used for various food stuffs or for agricultural chemicals, it is a preferable embodiment to use a polyhydric alcohol/fatty acid ester type surface active agent such as a sucrose/fatty acid ester, a glycerol/fatty acid ester, and/or lecithin, in combination with the protein partial degradation product. In that case, it is more preferable to use the protein partial degradation product and the surface active agent in a ratio of 6:1–1:6 (by weight), preferably 4:1–1:4, which gives a synergistic dispersing effect. Further, conventionally used preservatives such as ethanol, propionic acid, lactic acid, sorbic acid, dehydroacetic acid, butyl p-hydroxybenzoate, sodium chloride, etc., may be used in combination with the protein partial degradation product, this being also a preferred embodiment.

EXAMPLE

The present invention is explained in detail by the following Examples and Tests.

Examples 1 to 7 (Preparation of Partial Degradation of Wheat Gluten by Treatment with Alkali)

Twenty grams of wheat gluten (a reagent from Wako Pure Chemicals Co., Ltd., JAPAN) were added to each of 7 flasks containing 100 g of an aqueous solution of sodium hydroxide in the range of 0.2 to 4 g. Each of the mixtures was fully mixed under stirring and heated at a temperature of 80° C. to 150° C. for a period of 30 to 60 minutes. Each of the mixtures was neutralized by hydrochloric acid and diluted with pure water inter a total weight of 200 g to obtain Test samples 1 to 7 of the present invention.

Conditions for partial degradation and average molecular weights (as Mw measured by Gel Filtration Method) of the degradation products are shown in Table 1.

TABLE 1

| Test sample No. | Addition of NaOH (g) | Temperature (°C.) | Time (min) | Average molecular weight (Mw) |
|---|---|---|---|---|
| 1 | 0.2 | 80 | 30 | 101,000 |
| 2 | 0.5 | 80 | 30 | 80,500 |
| 3 | 1 | 80 | 30 | 72,000 |
| 4 | 1 | 100 | 60 | 61,000 |
| 5 | 2 | 100 | 60 | 47,000 |
| 6 | 4 | 100 | 60 | 20,200 |
| 7 | 4 | 150 | 360 | 1,300 |

Examples 8 to 10 (Preparation of Partial Degradation Products of Wheat Gluten by Treatment with Acid)

Twenty grams of the same wheat gluten as used in Example 1 were added to each of flasks containing 100 g of hydrochloric acid equivalent to 1 g, 2 g or 4 g of hydrogen chloride. Each of the mixtures was heated to 100° C. for minutes under stirring, neutralized by sodium hydroxide and diluted with pure water into a total weight of 200 g to obtain Test samples 8 to 10 of the present invention.

Conditions for partial degradation and average molecular weights of the degradation products are shown in Table 2.

TABLE 2

| Test sample No. | Addition of hydrochloric (g) | Temperature (°C.) | Time (min) | Average molecular weight (Mw) |
|---|---|---|---|---|
| 8 | 1 | 100 | 60 | 91,000 |
| 9 | 2 | 100 | 60 | 64,000 |
| 10 | 4 | 100 | 60 | 47,000 |

Example 11 (Preparation of a Partial Degradation Product of Wheat Gluten by Treatment with Enzyme)

Twenty grams of the same wheat gluten as used in Example 1 were added to a flask containing 150 g of 0.1N hydrochloric acid to obtain an aqueous solution of pH 1.5. 0.2 g of pepsin was added to the solution. The mixture was warmed at 37° C. for 90 minutes, neutralized by sodium hydroxide and diluted with pure water into a total weight of 200 g to obtain Test sample 11 of the present invention having an average molecular weight of 60,000.

Example 12 (Preparation of a Partial Degradation Product by Treatment with Reducing Agent)

Twenty grams of the same wheat gluten as used in Example 1 were added to 100g of an aqueous solution containing 4 g of sodium sulfite. The mixture was stirred at 30° C. for 60 minutes and diluted with pure water into a total weight of 200 g to obtain Test sample 12 of the present invention having an average molecular weight of 79,000.

Example 13 (Preparation of a Partial Degradation Product of Wheat Gluten by Treatment with Oxidizing Agent)

Twenty grams of the same wheat gluten as used in Example 1 were added to 100 g of an aqueous solution containing 1 g of $H_2O_2$. The mixture was heated to 40° C. for 60 minutes under stirring and sodium thiosulfate equivalent to the remaining $H_2O_2$ was added for masking $H_2O_2$. The mixture was diluted with pure water into a total weight of 200 g to obtain Test sample 13 of the present invention having an average molecular weight of 67,000.

Example 14 (Preparation of a Partial Degradation Product of Maize Gluten by Treatment with Alkali)

Maize gluten (from Nihon Shokuhin Kako Co., Ltd., JAPAN) as the starting material was put into the same partial degradation treatment with alkali as that employed in Example 5, whereby Test sample 14 of the present invention having an average molecular weight of 25,600 was obtained.

Example 15 (Preparation of a Partial Degradation Product of Soya Bean Protein by Treatment with Alkali)

Using a soya bean protein prepared by defatting a commercially available dried soya bean curd with acetone, as a starting material, the partial degradation treatment with alkali were performed under the same condition as that employed in Example 5, whereby Test sample 15 having an average molecular weight of 24,000 was obtained.

Example 16 (Preparation of a Partial Degradation Product of Wheat Gluten Treated with Acid, followed with Reducing Agent)

Fifty grams of a pure water solution containing 2 g of sodium sulfite (a reducing agent) were added to 100 g of a 10% aqueous solution of a partial degradation product of wheat gluten obtained by treatment with acid under the same condition as in Example 8. The mixture was warmed at 30° C. for 60 minutes and diluted with pure water into a total weight to obtain Test sample 16 having an average molecular weight of 53,000.

Example 17 (Preparation of a Partial Degradation Product of Wheat Gluten Treated with Acid, Followed with Enzyme)

A reagent of hydrochloric acid was added to 100 g of a 10% aqueous solution of a partial degradation product of wheat gluten obtained by treatment with acid under the same condition as in Example 8 to obtain an aqueous solution of pH 1.5. 0.1 g of pepsin was added to the solution. The mixture was warmed at 37° C. for 90 minutes, neutralized by sodium hydroxide and diluted with pure water into a total weight of 200 g to obtain Test sample 17 of the present invention having an average molecular weight of 46,000.

Example 18 (Preparation of a Partial Degradation Product of Wheat Gluten Treated with Reducing Agent Followed with Enzyme)

A reagent of hydrochloric acid was added to 100 g of a 10% aqueous solution of a partial degradation product of wheat gluten obtained by treatment with reducing agent under the same condition as in Example 12 to obtain an aqueous solution of pH 1.5. 0.1 g of pepsin was added to the solution. The mixture was warmed at 37° C. for 90 minutes, neutralized by sodium hydroxide and diluted with pure water into a total weight of 200 g to obtain Test sample 18 of the present invention having an average molecular weight of 35,000.

The following Tests were carried out on Test samples and Comparative test samples of the present invention.

Test 1 (Test of the Property which Decreases Viscosity of Calcium Carbonate Slurry)

Test Method

A total weight of 260 g of a Test sample of the present invention and city water was put into the National M1 type mixer and 250 g of calcium carbonate (light calcium carbonate from Takehara Kagaku Kogyo Co., Ltd., JAPAN) were added. The mixture was mixed for 2 minutes to obtain a 50% by weight slurry.

The slurry was transferred in a beaker and its viscosity was determined using the DVH-B type viscometer from TOKYO KEIKI CO., LTD., JAPAN.

Test 2 (Test of the Property which Decreases Viscosity of Kaolin Slurry).

A total weight of 200 g of a Test sample and city water was put into the National M1 type mixer and 300 g of kaolin in the form of powder (from Tsuchiya Kaolin Kogyo Co., Ltd., JAPAN) were added. The resultant slurry was mixed for 2 minutes to obtain a 50% by weight slurry.

The slurry was transferred in a beaker and its viscosity was determined using the DVH-B type viscometer from TOKYO KEIKI CO., LTD., JAPAN. The test results are shown in Table 3. The symbols of W, C and B shown in Table 3 mean wheat gluten, maize gluten and soya bean protein, respectively and the blanks in Table 3 mean "not measured" or "not tested".

TABLE 3

| Test sample * | Material | Average molecular weight | Particle dispersing property | |
|---|---|---|---|---|
| | | | Calcium carbonate slurry (cps) | Kaolin slurry (cps) |
| 1 | W | 101000 | 7900 | 6800 |
| 2 | W | 80500 | 3920 | 6200 |
| 3 | W | 72000 | 2970 | 4300 |
| 4 | W | 61000 | 925 | 4200 |
| 5 | W | 47000 | 708 | 2900 |
| 6 | W | 20200 | 471 | 198 |
| 7 | W | 1300 | 1856 | 1928 |
| 8 | W | 91000 | 214 | >8000 |
| 9 | W | 64000 | 194 | >8000 |
| 10 | W | 47000 | 936 | >8000 |
| 11 | W | 60000 | 896 | >8000 |
| 12 | W | 79000 | 878 | >8000 |
| 13 | W | 67000 | 2650 | |
| 14 | C | 25600 | 180 | 1750 |
| 15 | B | 24000 | 1010 | 780 |
| 16 | W | 53000 | 160 | 6800 |
| 17 | W | 46000 | 380 | 3900 |
| 18 | W | 35000 | | 4900 |
| Comparative test sample 1 | | | 5860 | 4782 |
| Comparative test sample 2 | | | 8000 | >8000 |
| Not added | — | — | 8000 | >8000 |

Note: Comparative test samples 1 and 2 are a sucrose fatty acid ester from DAI-ICHI KOGYO SEIYAKU CO., LTD., Japan [trade name, DK ester F-160 (HLB:15)] and a soyabean lecithin from Honen Seiyu Co., Ltd., Japan [trade name, Honen lecithin AY], respectively.
*0.3 g of the sample was used for each case.

It can be seen from the above test results that Test samples of the present invention produce an excellent particle dispersing effect.

Test 3 (Test of Dispersibility of Calcium Carbonate in milk)

Test Method

Powders (2 g) of calcium carbonate (trade name: COLLO-SALSO-TS, produced by SHIRAISHI CALCIUM KAISHA, LTD.) and a predetermined amount of test samples were added to 190 g of milk in a beaker with a capacity of 300 ml, and further tap water was added thereto until a total weight is 200 g (the concentration of calcium carbonate was 1%). This mixture was stirred for one minute by a mixer: the National M1 type mixer, then put into a cylinder having a capacity of 100 ml and left to stand for 24 hours. A part of the mixture (10 ml) around a level of 50 ml was taken and filtered. A residue (CaCO₃) on the filter paper was dissolved in hydrochloric acid and then subjected to atomic-absorption spectroscopy to measure a concentration of calcium therein. A concentration of calcium carbonate in the dispensed mixture was calculated from a measurement obtained in the above manner.

Another concentration of calcium carbonate prior to standing was similarly measured. Dispersibility of calcium carbonate particles was calculated from the concentrations of the former calcium carbonate and the latter calcium carbonate without standing by the following formula:

TABLE 4

| Test sample | Dispersibility (%) | | |
|---|---|---|---|
| | 0.1% of sample concentration | 0.05% of sample concentration | 0.02% of sample concentration |
| 1 | 30.7 | N.T. | N.T. |
| 2 | 38.4 | N.T. | N.T. |
| 3 | 41.5 | N.T. | N.T. |
| 4 | 54.4 | N.T. | N.T. |
| 5 | 57.4 | N.T. | N.T. |
| 6 | 61.9 | N.T. | N.T. |
| 7 | 46.7 | N.T. | N.T. |
| 8 | 80.6 | N.T. | N.T. |
| 9 | 91.7 | 70.5 | 52.0 |
| 10 | 74.3 | N.T. | N.T. |
| 11 | 54.8 | N.T. | N.T. |
| 12 | 45.0 | N.T. | N.T. |
| 13 | 42.8 | N.T. | N.T. |
| 14 | 82.5 | N.T. | N.T. |
| 15 | 53.4 | N.T. | N.T. |
| 16 | 83.8 | N.T. | N.T. |
| 17 | 74.3 | N.T. | N.T. |
| 18 | 87.8 | N.T. | N.T. |
| Comparative sample 1 | 14.0 | N.T. | N.T. |
| Comparative sample 2 | 5.5 | N.T. | N.T. |
| Not added | 0.5 | N.T. | N.T. |

Test sample Nos and Comparative sample Nos mean the same as in table 3.

Test 4 (Effect on Dispersibility of Solid Materials of Instant Miso)

Test Method

A commercially available instant miso powder ("Asage" from Kabushiki Kaisha Nagatanien Honpo, JAPAN) was first removed separated from its dried additives such as dried vegetables. To 10 g of the resultant powder was added a predetermined amount of a Test sample of the present invention. The mixture was fully mixed and put in a 200 ml measuring cylinder. 180 ml of boiled water were added under stirring and left to stand. After standing for 15 minutes the appearance and the settling state of the above mixture were observed.

Test samples were used in this test after they were filtered by using a filter (trade name: Ultrafilter 0 0010 076 E from Advantec Toyo Co., Ltd., JAPAN) to remove substances having a molecular weight smaller than 1,000 and then spray-dried using the Yamato Model GB-21 spray-dryer.

Comparative test samples used in this test are the same ones as used in Tests 1 and 2.

Test Results The results are shown in Table 5. The symbols of evaluation criteria in Table 6 have the following means.

⊙ ... Scarcely settles (<10 V/V %)
○ ... Slightly settles (10 to 30 V/V %)
△ ... Almost settles (30 to 50 V/V %)   × ... Completely settles (>50 V/V %)

TABLE 5

| Sample | Concentration of the sample with respect to miso powder (% by weight) | Evaluation |
|---|---|---|
| Test sample 4 | 2 | ○ |
| Test sample 8 | 2 | △ |
| Test sample 11 | 2 | ○ |
| Test sample 4 | 0.5 | △ |
| Test sample 14 | 2 | ○ |
| Test sample 16 | 2 | ○ |

TABLE 5-continued

| Sample | Concentration of the sample with respect to miso powder (% by weight) | Evaluation |
| --- | --- | --- |
| Test sample 4 | 1.6 + 0.4 | ⊚ |
| + | 1 + 1 | ⊚ |
| Comparative test sample 1 | 0.4 + 1.6 | ○ |
| Test sample 4 | 1.6 + 0.4 | ⊚ |
| + | 1 + 1 | ⊚ |
| Comparative test sample 2 | 0.4 + 1.6 | △ |
| Not added | — | X |
| Comparative test sample 1 | 0.5 | X |
|  | 2 | △ |
| Comparative test sample 2 | 2 | X |

Consideration

It can be seen from the results in Table 4 that Test samples of the present invention have an excellent effect on the dispersibility of the instant miso powder and further a combination use of a Test sample of the present invention and sucrose fatty acid ester or soya bean lecithin not only has an excellent effect on the same but also shows a synergistic effect.

Test 5 (Effect on Dispersibility of Cocoa)

Test Method

A prescribed amount of a Test sample was added to 5 g of a commercially available cocoa powder (Van Houten cocoa containing 22 to 24% of cocoa butter). The mixture was fully mixed and poured into a 100 ml graduated cylinder containing 95 g of cold water at 5° C. The cylinder was turned upside down 20 times and then left at room temperature for 10 minutes. The floating portion of the added cocoa was removed and its weight was measured. The dispersibility of cocoa was expressed by the value of the percentage of the cocoa dispersing in water, which can be calculated from the weight values of the added cocoa and its floating portion. The results are shown in Table 5.

TABLE 6

| Sample | Concentration of the sample with respect to cocoa (% by weight) | Dispersibility (%) |
| --- | --- | --- |
| Test sample 2 | 0.3 | 67 |
| Test sample 10 | 0.3 | 79 |
| Test sample 11 | 0.3 | 77 |
| Test sample 12 | 0.3 | 68 |
| Test sample 13 | 0.3 | 75 |
| Test sample 15 | 0.3 | 72 |
| Test sample 17 | 0.3 | 79 |
| Test sample 17 | 0.24 + 0.06 | 82 |
| + | 0.15 + 0.15 | 85 |
| Palmitic acid monoglyceride | 0.06 + 0.24 | 73 |
| Not added | — | 48 |
| Comparative test sample 1 | 0.3 | 67 |
| Palmitic acid monoglyceride | 0.3 | 62 |

Note: i) Comparative test sample 1 is the same one as used in Tests 1 and 2.
ii) The palmitic acid monoglyceride used in this test is the one of trade name Sunsoft No. 8001 from Taiyo Kagaku co., Ltd., Japan.

Consideration

It can be seen from the results in Table 5 that Test sample of the present invention are excellent as dispersing agents improving the dispersibility of cocoa and further a combination use of a Test sample and palmitic acid monoglyceride synergistically improves the dispersibility of cocoa.

Test 6

A test sample or a Comparative test sample was dispersed or dissolved in city water. The resultant was put into a ball mill and Tsumacide (m-tolylmethylcarbamate) of a solid insecticide, DCPA (3′,4′-dichloropropionanilide) of a solid herbicide or MBTC (methylene bisthiocyanate) of a solid bactericide was added. Glass beads of 1 mm diameter were put into the ball mill and the mixture was water-ground for 8 hours to obtain the preparations 1 to 17. Comparative test samples 1 and 2 are the same ones as used in Tests 1 and 2.

Stability Test

A preparation was put into a 50 ml measuring cylinder. After it was left to stand at 25° C. for 4 weeks, the settling rate of the preparation which shows its stability was measured. Conditions for preparing the preparations and the test results are shown in Table 6.

TABLE 7

| Preparation No. | 1 | 2 | 3 | 4 | 5 | 6 | 7 |
| --- | --- | --- | --- | --- | --- | --- | --- |
| Tested agent | | | | | | | |
| Tsumacide | 45 | 45 | 45 | 45 | 45 | 45 | 45 |
| Test sample | | | | | | | |
| Test sample 4 | 2 | | | | | | |
| Test sample 8 | | 2 | | | | | |
| Test sample 15 | | | 2 | | | | |
| Test sample 18 | | | | 2 | | | |
| Comparative test sample 1 | | | | | 5 | | |
| Comparative test sample 2 | | | | | | 5 | |
| Water | 53 | 53 | 53 | 53 | 50 | 50 | 55 |
| Stability test | | | | | | | |
| Settling rate (%) | 78 | 74 | 85 | 88 | 73 | 67 | 68 |
| Viscosity (25° C.) c.p. | | | | | | | |
| Immediately after preparing | 315 | 320 | 240 | 225 | 380 | 488 | 490 |
| After standing | 318 | 322 | 242 | 230 | 396 | 500 | 506 |

| Preparation No. | 8 | 9 | 10 | 11 |
| --- | --- | --- | --- | --- |
| Tested agent | | | | |
| DCPA | 40 | 40 | 40 | 40 |
| Test sample | | | | |
| Test sample 2 | 2 | | | |
| Test sample 14 | | 2 | | |
| Test sample 17 | | | 2 | |
| Water | 58 | 58 | 58 | 60 |
| Settling test | | | | |
| Settling rate (%) | 81 | 86 | 89 | 70 |
| Viscosity (25° C.) c.p. | | | | |
| Immediately after preparing | 220 | 187 | 170 | 460 |
| After standing | 224 | 188 | 172 | 480 |

| Preparation No. | 12 | 13 | 14 | 15 | 16 | 17 |
| --- | --- | --- | --- | --- | --- | --- |
| Tested agent | | | | | | |
| MBTC | 15 | 15 | 15 | 15 | 15 | 15 |
| Test sample | | | | | | |
| Test sample 5 | 3 | | | | | |
| Test sample 9 | | 3 | | | | |
| Test sample 11 | | | 3 | | | |
| Comparative test sample 1 | | | | 5 | | |
| Comparative test sample 2 | | | | | 5 | |
| Water | 82 | 82 | 82 | 80 | 80 | 85 |
| Settling rate (%) | 68 | 64 | 62 | 37 | 45 | 30 |

The settling rate is calculated using the following formula.

$$\text{Settling rate (\%)} = \frac{\text{Height of the initial preparation} - \text{Height of the supernatant after standing}}{\text{Height of the initial preparation}} \times 100$$

Of all of the preparations except the preparations containing MBTC as a agent to be tested, their viscosities were also determined immediately after preparing and after standing.

Test 7

Two portions of a 2,000 ppm aqueous solution of each of Test samples of the present invention and such conventional surface active agents as sodium dodecylbenzenesulfonate, lauryltrimethylammonium chloride and polyoxyethylenenonylphenylether (n=10) were separately sprayed to a young seedling of tomato grown for about 25 days after seeding. The young seedlings were kept in a humid atmosphere for 6 days and the degree of damage to them from the sprayed agents was observed. The results are shown in Table 7.

Test samples of the present invention used are the ones desalted and dried as in Test 3.

TABLE 8

| Sample | Degree of damage of young tomato seedlings |
|---|---|
| Not added | — |
| Test sample 5 | — |
| Test sample 9 | — |
| Test sample 11 | — |
| Test sample 14 | — |
| Test sample 16 | — |
| Test sample 17 | — |
| Sodium dodecyl-benzenesulfonate | ± |
| Lauryltrimethyl-ammonium chloride | ++ |
| Polyoxyethylene-nonylphenylether (n = 10) | + |

Note
—: No damage
±: The edges of some leaves died.
+: Some leaves changed color to brown.
++: Many leaves changed color to brown.

What is claimed is:

1. A method for forming a stabilized dispersion in an aqueous medium of water insoluble inorganic and/or organic particle additives for food stuffs, said method comprising mixing said inorganic and/or organic particle additives with from 0.2%–20% by weight of said inorganic and/or organic particle additives of a grain protein partial degradation product which acts as a particle dispersing agent in said aqueous medium to form a stabilized aqueous dispersion of said inorganic and/or organic particle additives, said grain protein partial degradation product having a weight average molecular weight of from 500 to 110,000, and being obtained by subjecting a grain protein to:
   (i) a single degradative treatment with a degradation agent selected from the group consisting of alkali, acid, proteinase, reducing agent, and oxidizing agent, or
   (ii) a combination of degradative treatments with two degradative agents selected from the group consisting of acid, proteinase, reducing agent and oxidizing agent.

2. The method of claim 1, in which the grain protein is selected from the group consisting of wheat gluten, maize gluten and soya bean protein.

3. The method of claim 1, in which the grain protein partial degradation product has a weight average molecular weight of between 700 and 100000.

4. The method of claim 1, in which the grain protein partial degradation product is prepared by degradation of the grain protein with alkali in a dilute aqueous alkaline solution at a temperature of 60° to 180° C. for a period of 10 to 600 minutes.

5. The method of claim 1, in which the grain protein partial degradation product is prepared by degradation of the grain protein with acid in a dilute aqueous acid solution at a temperature of 60° to 120° C. for a period of 10 to 600 minutes.

6. The method of claim 1, in which the grain protein partial degradation product is prepared by degradation of the grain protein with proteinase in an aqueous solution of an enzyme having protease activity at a temperature of up to 60° C. for a period of 60 to 600 minutes.

7. The method of claim 1, in which the grain protein partial degradation product is prepared by degradation of the grain protein with a reducing agent in a dilute aqueous solution of a reducing agent at a temperature of 10° to 100° C. for a period of 10 to 600 minutes.

8. The method of claim 1, in which the grain protein partial degradation product is prepared by degradation of the grain protein with an oxidizing agent in a dilute aqueous solution of an oxidizing agent at a temperature of 10° to 100° C. for a period of 10 to 600 minutes.

9. The method of claim 1, wherein the water insoluble organic particle additives are selected from the group consisting of cocoa powder, fruit pulp, miso, and instant soup.

10. The method of claim 1, wherein the water insoluble inorganic and/or organic particle additives contain calcium.

* * * * *